US 11,766,313 B2

(12) United States Patent
Li et al.

(10) Patent No.: US 11,766,313 B2
(45) Date of Patent: *Sep. 26, 2023

(54) METHODS FOR MAKING DENTAL ALIGNERS FROM MULTILAYER SHEETS

(71) Applicant: ALIGN TECHNOLOGY, INC., San Jose, CA (US)

(72) Inventors: Chunhua Li, Cupertino, CA (US); Yan Chen, Cupertino, CA (US); Heinz Pudleiner, Krefeld (DE); Klaus Meyer, Dormagen (DE); Joerg Nickel, Dormagen (DE); Craig Pehlert, Lenox, MA (US)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/107,736

(22) Filed: Feb. 9, 2023

(65) Prior Publication Data
US 2023/0190414 A1    Jun. 22, 2023

Related U.S. Application Data

(60) Continuation of application No. 17/902,445, filed on Sep. 2, 2022, now Pat. No. 11,648,091, which is a
(Continued)

(51) Int. Cl.
*A61C 7/08* (2006.01)
*B32B 27/28* (2006.01)
(Continued)

(52) U.S. Cl.
CPC .............. *A61C 7/08* (2013.01); *B29C 51/14* (2013.01); *B32B 7/022* (2019.01); *B32B 25/08* (2013.01);
(Continued)

(58) Field of Classification Search
None
See application file for complete search history.

(56) References Cited

U.S. PATENT DOCUMENTS 4,253,828 A * 3/1981 Coles ................. A61C 7/00
433/6
4,410,595 A * 10/1983 Matsumoto ............ B32B 27/34
428/424.4
(Continued)

FOREIGN PATENT DOCUMENTS

CN    103374211 A  * 10/2013
CN    108394152 A  *  8/2018
(Continued)

OTHER PUBLICATIONS

"Overview of Materials for PETG Copolyester" (http://www.matweb.com/search/DataSheet.aspx?MatGUID=4de1c85bb946406a86c52b688e3810d0&ckck=1) (webpage retrieved on Oct. 27, 2020) (Year: 2020).*
(Continued)

*Primary Examiner* — Vivian Chen
(74) *Attorney, Agent, or Firm* — Wilson Sonsini Goodrich & Rosati

(57) ABSTRACT

A multilayer sheet comprising first, second, and third layers is provided. The first layer consists of a co-polyester having an elongation at break of greater than 70%. The second layer consists of a thermoplastic polyurethane elastomer having an elongation at break of greater than 200% and a hardness of about 60 A to about 85 D. The first layer has a hardness greater than the hardness of the second layer. A mold is provided and the multilayer sheet is thermoformed over the mold to form a plurality of tooth-receiving cavities configured to receive and position a patient's teeth from a first arrangement toward a second arrangement. Excess material
(Continued)

is trimmed from the thermoformed multilayer sheet to form the multilayer dental aligner.

30 Claims, 8 Drawing Sheets

Related U.S. Application Data continuation of application No. 17/858,825, filed on Jul. 6, 2022, now Pat. No. 11,648,090, which is a continuation of application No. 17/553,590, filed on Dec. 16, 2021, which is a continuation of application No. 16/835,101, filed on Mar. 30, 2020, now Pat. No. 11,213,369, which is a continuation of application No. 15/476,655, filed on Mar. 31, 2017, now Pat. No. 10,973,613, which is a division of application No. 13/470,681, filed on May 14, 2012, now Pat. No. 9,655,691.

(51) Int. Cl.

| | |
|---|---|
| B32B 7/022 | (2019.01) |
| B32B 25/08 | (2006.01) |
| B32B 25/20 | (2006.01) |
| B32B 27/08 | (2006.01) |
| B32B 27/30 | (2006.01) |
| B32B 27/32 | (2006.01) |
| B32B 27/34 | (2006.01) |
| B32B 27/36 | (2006.01) |
| B32B 27/40 | (2006.01) |
| B29C 51/14 | (2006.01) |
| B32B 25/14 | (2006.01) |
| A61C 13/00 | (2006.01) |
| A61F 5/56 | (2006.01) |
| A61C 19/06 | (2006.01) |
| A61C 7/00 | (2006.01) |
| A63B 71/08 | (2006.01) |
| B29K 67/00 | (2006.01) |
| B29K 75/00 | (2006.01) |
| B29L 31/00 | (2006.01) |

(52) U.S. Cl.
CPC .............. *B32B 25/20* (2013.01); *B32B 27/08* (2013.01); *B32B 27/281* (2013.01); *B32B 27/285* (2013.01); *B32B 27/286* (2013.01); *B32B 27/308* (2013.01); *B32B 27/32* (2013.01); *B32B 27/34* (2013.01); *B32B 27/36* (2013.01); *B32B 27/365* (2013.01); *B32B 27/40* (2013.01); *A61C 7/00* (2013.01); *A61C 13/00* (2013.01); *A61C 19/06* (2013.01); *A61F 5/56* (2013.01); *A63B 71/085* (2013.01); *B29K 2067/00* (2013.01); *B29K 2075/00* (2013.01); *B29K 2995/007* (2013.01); *B29K 2995/0026* (2013.01); *B29K 2995/0077* (2013.01); *B29K 2995/0082* (2013.01); *B29L 2031/753* (2013.01); *B32B 25/14* (2013.01); *B32B 27/283* (2013.01); *B32B 27/30* (2013.01); *B32B 27/302* (2013.01); *B32B 2250/03* (2013.01); *B32B 2250/24* (2013.01); *B32B 2250/40* (2013.01); *B32B 2274/00* (2013.01); *B32B 2307/40* (2013.01); *B32B 2307/412* (2013.01); *B32B 2307/50* (2013.01); *B32B 2307/51* (2013.01); *B32B 2307/536* (2013.01); *B32B 2307/54* (2013.01); *B32B 2307/546* (2013.01); *B32B 2319/00* (2013.01); *B32B 2323/00* (2013.01); *B32B 2323/04* (2013.01); *B32B 2323/10* (2013.01); *B32B 2323/16* (2013.01); *B32B 2333/04* (2013.01); *B32B 2367/00* (2013.01); *B32B 2371/00* (2013.01); *B32B 2375/00* (2013.01); *B32B 2377/00* (2013.01); *B32B 2383/00* (2013.01); *B32B 2535/00* (2013.01); *B32B 2555/00* (2013.01); *Y10T 428/31551* (2015.04); *Y10T 428/31565* (2015.04); *Y10T 428/31786* (2015.04)

(56) References Cited

U.S. PATENT DOCUMENTS

| | | | | |
|---|---|---|---|---|
| 4,739,012 A | * | 4/1988 | Hagman | C08L 27/06 525/166 |
| 4,755,139 A | * | 7/1988 | Abbatte | A61C 7/08 433/6 |
| 4,843,124 A | * | 6/1989 | Wolfe, Jr. | C08L 11/00 525/173 |
| 5,335,675 A | * | 8/1994 | Wheeler | B29C 49/00 128/842 |
| 6,077,075 A | * | 6/2000 | Bedard | A61C 13/04 433/167 |
| 6,454,565 B2 | * | 9/2002 | Phan | B29C 48/154 433/6 |
| 6,746,757 B1 | * | 6/2004 | Takagi | B32B 27/34 428/476.3 |
| 7,201,575 B2 | * | 4/2007 | Adell | A61C 13/0001 433/80 |
| 7,641,828 B2 | * | 1/2010 | DeSimone | A61C 7/08 264/16 |
| 8,758,009 B2 | | 6/2014 | Chen et al. | |
| 8,905,756 B2 | | 12/2014 | Schwartz | |
| 9,655,691 B2 | * | 5/2017 | Li | B32B 7/022 |
| 9,655,693 B2 | * | 5/2017 | Li | B32B 27/40 |
| 10,052,176 B2 | * | 8/2018 | Li | A61C 7/08 |
| 10,973,613 B2 | * | 4/2021 | Li | B32B 27/34 |
| 11,109,946 B2 | * | 9/2021 | Venkatasanthanam | .. A61C 7/08 |
| 11,154,384 B2 | * | 10/2021 | Li | B32B 7/022 |
| 11,213,369 B2 | * | 1/2022 | Li | B32B 27/34 |
| 11,576,753 B2 | * | 2/2023 | Li | B29C 51/14 |
| 2002/0146549 A1 | * | 10/2002 | Kranenburg-Van Dijk | B32B 27/06 428/480 |
| 2004/0146670 A1 | * | 7/2004 | Chin | B29C 48/13 428/35.2 |
| 2004/0224283 A1 | | 11/2004 | Sun et al. | |
| 2005/0082703 A1 | * | 4/2005 | Wrosz | B29C 51/22 264/16 |
| 2005/0100853 A1 | * | 5/2005 | Tadros | A61C 19/063 433/6 |
| 2006/0078688 A1 | * | 4/2006 | DeSimone | A61C 7/08 264/494 |
| 2006/0078841 A1 | * | 4/2006 | DeSimone | A61C 7/08 433/6 |
| 2007/0087300 A1 | * | 4/2007 | Willison | A61C 7/12 433/6 |
| 2008/0044786 A1 | * | 2/2008 | Kalili | A61C 7/08 433/6 |
| 2008/0248438 A1 | * | 10/2008 | DeSimone | A61C 7/08 433/6 |
| 2009/0061380 A1 | * | 3/2009 | Yamamoto | A61C 7/20 433/18 |
| 2009/0130624 A1 | | 5/2009 | Sun et al. | |
| 2009/0298006 A1 | * | 12/2009 | Schwartz | A61C 7/08 433/34 |
| 2011/0020761 A1 | * | 1/2011 | Kalili | A61C 7/08 433/214 |
| 2011/0039223 A1 | * | 2/2011 | Li | B29C 45/0001 264/16 |
| 2012/0101417 A1 | * | 4/2012 | Joseph | B29C 51/00 602/5 |
| 2012/0315484 A1 | * | 12/2012 | Riedl | B29C 48/307 156/306.6 |
| 2015/0374464 A1 | * | 12/2015 | Stewart | C09K 11/06 264/16 |

(56) References Cited

U.S. PATENT DOCUMENTS

| | | | |
|---|---|---|---|
| 2019/0159870 A1* | 5/2019 | Li | B32B 27/40 |
| 2019/0183611 A1* | 6/2019 | Li | B32B 27/40 |
| 2019/0231484 A1* | 8/2019 | Li | B32B 25/20 |
| 2021/0078357 A1* | 3/2021 | Venkatasanthanam | A61C 13/0006 |
| 2022/0249203 A1* | 8/2022 | Li | B32B 25/20 |
| 2022/0287803 A1* | 9/2022 | Li | B32B 27/36 |
| 2022/0338957 A1* | 10/2022 | Li | B32B 27/365 |

FOREIGN PATENT DOCUMENTS

| | | | |
|---|---|---|---|
| DE | 102010036107 A * | 3/2012 | |
| WO | WO 2006/096558 A2 * | 9/2006 | |
| WO | WO 2010/043419 A * | 4/2010 | |
| WO | WO-2010043419 A1 | 4/2010 | |
| WO | WO-2013130552 A1 | 9/2013 | |

OTHER PUBLICATIONS

"TEXIN 990R—Thermoplastic Polyurethane" (2002) (Year: 2002).*
"Shore A Hardness Scale" (https://www.cuttosize.com.au/technical-support/shore-hardness-scale/) (webpage retrieved Nov. 18, 2022) (undated) (Year: 2022).*
Allcock, et al. Condensation and Other Step-Type Polymerizations. Chapter 2. Contemporary Polymer Chemistry. Second Edition. Simon & Schuster. 1981. pp. 29-30, 43 (6 pages).
Beer, et al. Bending of Members Made of Several Materials. Chapter 4.6. Mechanics of Materials. Third Edition. McGraw Hill. 2001. p. 231 (9 pages).
Callister W.D. Jr. Glossary definitions. Materials Science and Engineering an Introduction. Third Edition. John Wiley & Sons, Inc. 1985. p. 776. (4 pages).
Campo E.A. Tensile Stress-Strain Behavior. Ch. 2.2.1. Flexural Strength. Ch. 2.2.2. Selection of Polymeric Materials: How to Select Design Properties from Different Standards. PDL Handbook Series. William Andrew Inc. 2008. pp. 50-51 (17 pages).
Diaconu, et al. Properties of Polyurethane Thin Films. Journal of Optoelectronics and Advanced Materials. 2005. vol. 7 (2): 921-924.
Mix, et al. Standardized Polymer Durometry. Journal of Testing and Evaluation. 2011. vol. 39 (4): 696-705.
Painter, et al. Mechanical and Rheological Properties. Chapter 13. Essentials of Polymer Science and Engineering. DEStech Publications, Inc. 2009. pp. 399-471 (86 pages).
Qi, et al. Durometer Hardness and the Stress-Strain Behavior of Elastomeric Materials. Rubber Chemistry and Technology. May 1, 2003. vol. 76 (2): 419-435. doi:https://doi.org/10.5254/1.3547752.
Qi, et al. Stress-strain behavior of thermoplastic polyurethanes. Mechanics of Materials. Aug. 2005. vol. 37(8): 817-839.
SCHEU Dental GmbH. DURASOFT® product data sheet. Revision 2 18/14. Aug. 2014. German language. English Translation provided. (6 pages).
YAM. Sheet, PETG. The Wiley Encyclopedia of Packaging Technology. Third Edition. John Wiley & Sons, Inc. 2009. pp. 1096-1100 (14 pages).

* cited by examiner

METHODS FOR MAKING DENTAL ALIGNERS FROM MULTILAYER SHEETS

CROSS-REFERENCE

This application is a continuation of U.S. patent application Ser. No. 17/902,445, filed Sep. 2, 2022, now U.S. Pat. No. 11,648,091, issued May 16, 2023, which is a continuation of U.S. patent application Ser. No. 17/858,825, filed Jul. 6, 2022, now U.S. Pat. No. 11,648,090, issued May 16, 2023, which is a continuation of U.S. patent application Ser. No. 17/553,590, filed Dec. 16, 2021, which is a continuation of U.S. patent application Ser. No. 16/835,101, filed Mar. 30, 2020, now U.S. Pat. No. 11,213,369, issued Jan. 4, 2022, which is a continuation of U.S. patent application Ser. No. 15/476,655, filed Mar. 31, 2017, now U.S. Pat. No. 10,973,613, issued Apr. 13, 2021, which is a divisional of U.S. patent application Ser. No. 13/470,681, filed May 14, 2012, now U.S. Pat. No. 9,655,691 issued May 23, 2017, the entire contents of which are incorporated herein by reference.

BACKGROUND OF THE INVENTION

The present invention generally relates to the field of orthodontics, and more particularly to the design of multilayer dental positioning appliances.

An objective of orthodontics is to move a patient's teeth to positions where function and/or aesthetics are optimized. Traditionally, appliances such as braces are applied to a patient's teeth by a treating practitioner and the set of braces exerts continual force on the teeth and gradually urges them toward their intended positions. Over time and with a series of clinical visits and reactive adjustments to the braces by the practitioner, the appliances to move the teeth toward their final destination.

More recently, alternatives to conventional orthodontic treatment with traditional affixed appliances (e.g., braces) have become available. For example, systems including a series of preformed appliances/aligners have become commercially available from Align Technology, Inc., San Jose, Calif., under the trade name Invisalign® System. The Invisalign® System is described in numerous patents and patent applications assigned to Align Technology, Inc. including, for example in U.S. Pat. Nos. 6,450,807, and 5,975,893, as well as on the company's website, which is accessible on the World Wide Web (see, e.g., the url invisalign.com"). The Invisalign® System includes designing and/or fabricating multiple, and sometimes all, of the aligners to be worn by the patient before the aligners are administered to the patient and used to reposition the teeth (e.g., at the outset of treatment). Often, designing and planning a customized treatment for a patient makes use of computer-based 3-dimensional planning/design tools, such as Treat™ software from Align Technology, Inc. The design of the aligners relies on computer modeling of the patient's teeth in a series of planned successive tooth arrangements, and the individual aligners are designed to be worn over the teeth, such that each aligner exerts force on the teeth and elastically repositions the teeth to each of the planned tooth arrangements.

While recently developed orthodontic treatment technologies, such as those described above, represent a considerable advancement in the field of orthodontics, additional advancements remain of interest. For example, in some instances it may be advantageous to develop materials that improve properties of the appliances/aligners used for orthodontic treatment. As such, there is a need for shell aligners that can, for example, produce more continuous force and better bring a patient's teeth into a desired occlusion.

BRIEF SUMMARY OF THE INVENTION

The present invention provides multilayer orthodontic positioning appliances, as well as related methods and systems. The disclosed multilayer appliances include a removable orthodontic tooth positioning appliance having teeth receiving cavities shaped to directly receive at least some of the patient's teeth and apply a resilient positioning force to the patient's teeth. The multilayer appliances can include a hard polymer layer disposed between two soft polymer layers. The multilayer dental appliances of the present invention, among many aspects, provide, for example, improved material performance, stress relaxation properties and longer working range. In addition, the mechanical properties of the materials and appliances described herein can improve orthodontic treatments by, for example, reducing the need for midcourse corrections during treatment and the number of aligners used for a given treatment.

The disclosed methods include methods for making multilayer dental appliances. The disclosed systems including a plurality of appliances having teeth receiving cavities shaped to directly receive at least some of the patient's teeth and apply a resilient positioning force to the patient's teeth. The appliances can be successively worn by a patient to move teeth from one arrangement to a successive arrangement. At least one of the appliances in the system can include a hard polymer layer disposed between two soft polymer layers.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION OF THE INVENTION

Figure 1:
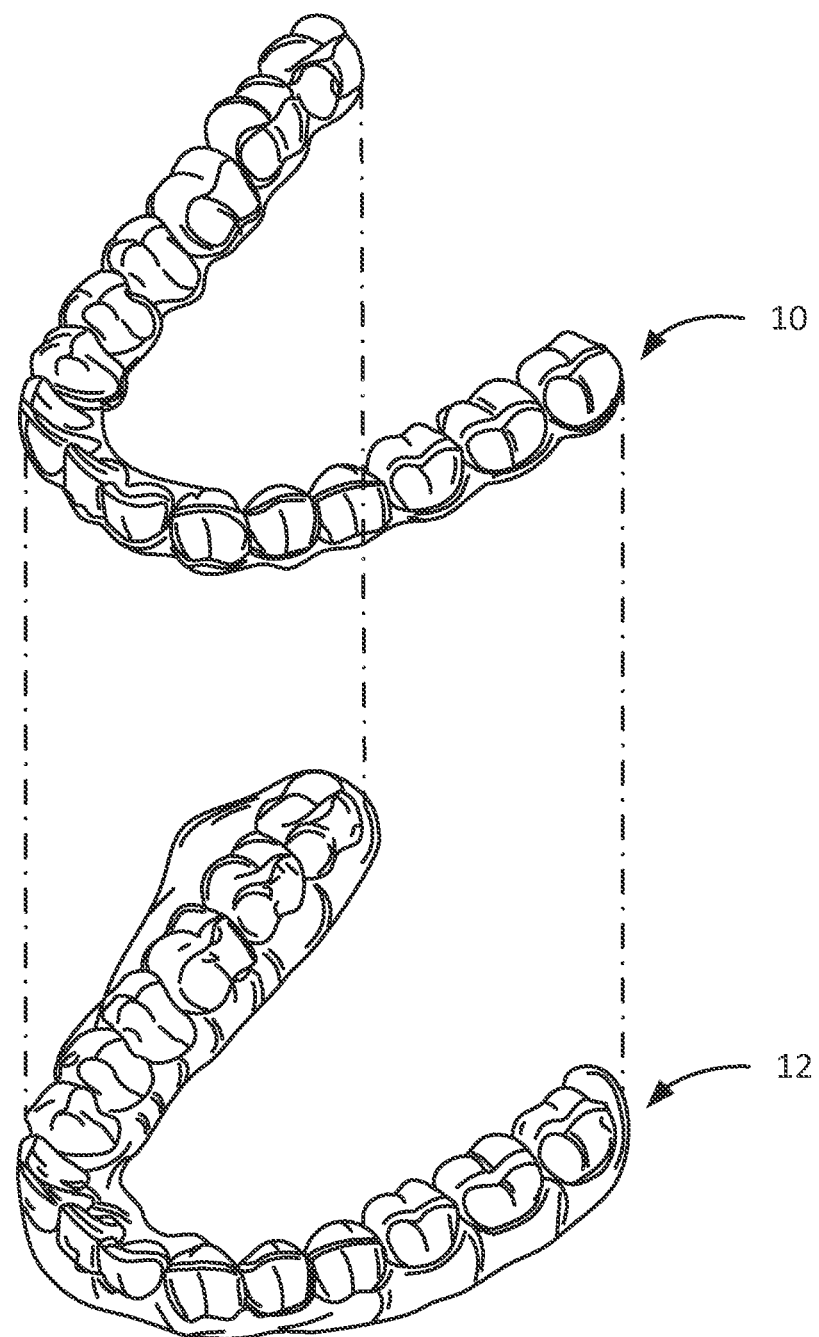
FIG. 1 illustrates a jaw and an incremental positioning appliance for the jaw, in accordance with an embodiment of the present invention.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Multilayer orthodontic positioning appliances are provided, as well as related methods and systems. During orthodontic treatment, it may be necessary to apply forces to a tooth to generate movement of the tooth to, for example, bring the patient's teeth into a better occlusion in a mesial or distal direction. The presently disclosed appliances, methods, and systems provide means by which such forces can be applied during orthodontic treatment where appliances having teeth receiving cavities are used, such as preformed appliances/aligners available from Align Technology, Inc., San Jose, Calif., under the trade name Invisalign® System. As provided by the present invention, the aligners that include multilayer sheets can, for example, provide increased durability of the aligners so that they can better withstand wear due to aligner reinsertion and removal and other mechanical stresses put on the aligner during treatment. In addition, the aligners have improved elastic properties that allow for less degradation in the shape of the teeth receiving cavities during a stage of treatment. For example, during a multistage orthodontic treatment, the force exerted by an aligner to perform defined tooth movement can degrade and may cause the treatment to include more aligners to reach a final ideal arrangement and/or result in a mid-course correction that could be prevented by using aligners with improved physical properties, such as those provided herein.

In one embodiment, the present invention provides a dental appliance for positioning a patient's teeth. The dental appliance can include a removable orthodontic tooth positioning appliance having teeth receiving cavities shaped to directly receive at least some of the patient's teeth and apply a resilient positioning force to the patient's teeth, the appliance comprising a hard polymer layer disposed between a first soft polymer layer and a second soft polymer layer.

In another embodiment, the present invention provides an orthodontic system for positioning a patient's teeth. The orthodontic system can include a plurality of incremental position adjustment appliances having teeth receiving cavities shaped to directly receive at least some of the patient's teeth and apply a resilient positioning force to the patient's teeth, wherein the appliances are successively worn by a patient to move teeth from one arrangement to a successive arrangement, and wherein at least one of the appliances comprises a hard polymer layer disposed between a first soft polymer layer and a second soft polymer layer.

In yet another embodiment, the present invention provides a method of making a dental appliance for positioning a patient's teeth. The method can include providing a sheet comprising a hard polymer layer of polymeric material disposed between a first soft polymer layer and a second soft polymer layer, providing a positive model of the patient's teeth in a target position; and fabricating an appliance as a negative of the positive model comprising thermoforming the sheet over the positive model.

Referring now to the drawings, in which like reference numerals represent like parts throughout the several views, FIG. 1 provides an appropriate starting point in a detailed discussion of various embodiments of the present invention with respect to tooth repositioning appliances designed to apply repositioning forces to teeth. A tooth repositioning appliance 10 can be worn by a patient in order to achieve an incremental repositioning of individual teeth in the jaw 12. The appliance can include a shell (e.g., a polymeric shell) having teeth-receiving cavities that receive and resiliently reposition the teeth. In many embodiments, a polymeric appliance can be formed from a sheet of suitable layers of polymeric material. An appliance can fit over all teeth present in an upper or lower jaw, or less than all of the teeth. In some cases, only certain teeth received by an appliance will be repositioned by the appliance while other teeth can provide a base or anchor region for holding the appliance in place as it applies force against the tooth or teeth targeted for repositioning. In some cases, many or most, and even all, of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual anchors on teeth with corresponding receptacles or apertures in the appliance so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url invisalign.com").

An appliance can be designed and/or provided as part of a set of a plurality of appliances. In such an embodiment, each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. A target tooth arrangement can be a planned final tooth arrangement selected for the patient's teeth at the end of all planned orthodontic treatment. Alternatively, a target arrangement can be one of many intermediate arrangements for the patient's teeth during the course of orthodontic treatment, which may include where surgery is recommended, where inter-proximal reduction (IPR) is appropriate, where a progress check is scheduled, where anchor placement is best, where palatal expansion is desirable, etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages. The adjustment appliances can be generated all at the same stage or in sets or batches, e.g., at the beginning of a stage of the treatment, and the patient wears each appliance until the pressure of each appliance on the teeth can no longer be felt or has resulted in the maximum amount of expressed tooth movement for that given stage. A plurality of different appliances (e.g., set) can be designed and even fabricated prior to the patient wearing any appliance of the plurality. After wearing an appliance for an appropriate period of time, the patient replaces the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

In general, structures, methods and systems of the present invention utilize a multilayer sheet for use in orthodontic appliances. The multilayer sheet can include three layers, in which a hard polymer layer is disposed between two soft polymer layers. The multilayer sheets used in the present invention can be used in making dental aligners having improved durability for use, e.g., to the elastic properties of the multilayer sheet when formed into an aligner. In addition, the bonding strength between the layers further improves the durability of the aligners, for example, by withstanding teeth grinding by a patient.

Figure 2:
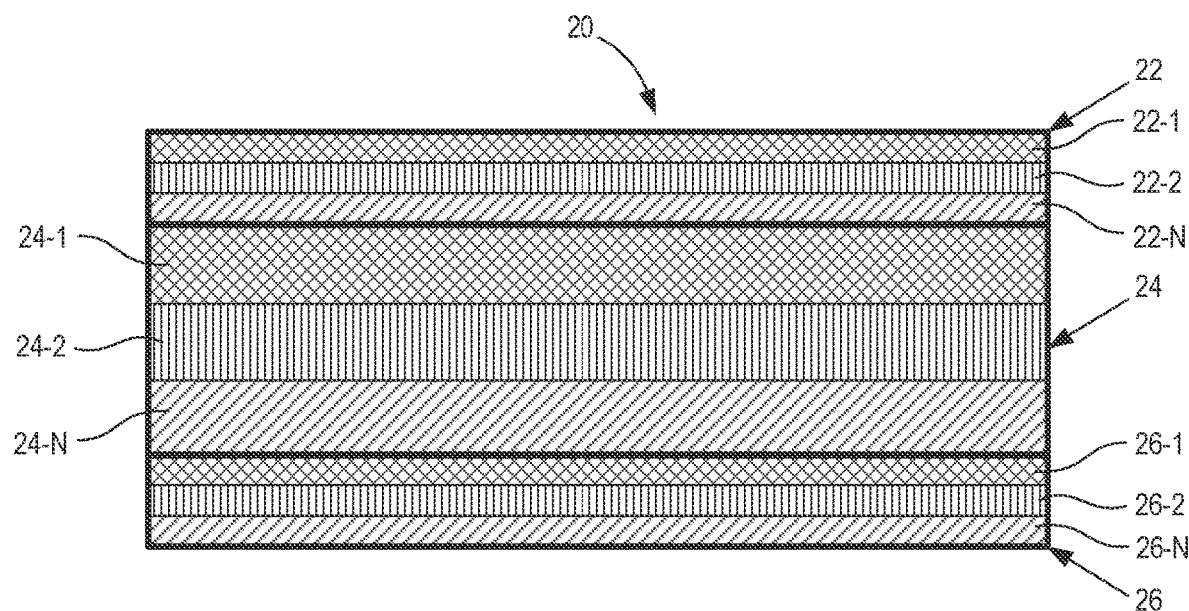
FIG. 2 shows an arrangement of polymer layers in a sheet having a hard polymer layer disposed between two soft polymer layers, in accordance with an embodiment of the present invention.

FIG. 2 shows a multilayer structure according to the present invention. As shown, a multilayer sheet 20 can include a three-layer structure: a hard polymer layer 24 and two soft polymer layers 22, 26. The hard polymer layer can be disposed between a first soft polymer layer and a second soft polymer layer. In some embodiments, the hard polymer layer can be thicker than either of the soft polymer layers. The soft polymer layers can have the same or different thicknesses. For example, the hard polymer layer can have a thickness in a range from about 400 µm to about 1100 µm, about 450 µm to about 1000 µm, about 500 µm to about 900 µm, or about 550 µm to about 750 µm. The soft polymer layers can have a thickness in a range from about 25 µm to about 100 µm, about 30 µm to about 90 µm, or about 35 µm to about 80 µm. Multilayer sheets used for making appliances having a hard polymer layer disposed between two soft polymer layers can range from a thickness of about 500 µm to about 1200 µm, about 550 µm to about 1100 µm, or about 600 µm to about 1000 µm. In some embodiments, the thicknesses of the various layers can be tailored for a particular stage of treatment for the patient.

Suitable polymeric materials for the hard polymer layer can include a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate or a combination thereof (e.g., a blend of at least two of the listed hard polymeric materials). In some embodiments, the hard polymer layer of the appliances can include polymeric materials, such as a polycarbonate, a co-polyester, a polyester, and a thermoplastic polyurethane. In some embodiments, the hard layer can be composed of multiple hard layers, e.g., two or three hard polymer layers 24-1, 24-2, 24-N co-extruded to form one hard layer.

The hard polymer layer of the appliances of the present invention can have a variety of physical properties that can, e.g., improve treatment options for a practitioner. For example, physical properties such as tensile strength, elongation at yield, elongation at break, tensile modulus, flexural modulus, stress relaxation over time, and light transmission can each be specifically tailored for a particular application. In some embodiments, the hard polymer layer of the appliances can have a physical property of at least one of a tensile strength at yield of between about 4000 pounds per square inch (psi) and 6500 psi, an elongation at yield of greater than about 4%, an elongation at break of greater than about 70%, a tensile modulus of greater than about 150,000 psi, a flexural modulus greater than about 150,000 psi, a stress relaxation at 24 hours testing in a wet environment (e.g., between about 90%-100% relative humidity) is greater than 10%, and a light transmission between 400 nm and 800 nm of greater than about 75%.

Suitable polymeric materials for the soft polymer layers of the appliance can include a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, or a combination thereof (e.g., a blend of at least two of the listed soft polymer materials). The soft polymer layers can be the same material or a different material. In certain embodiments, the first soft polymer layer and the second soft polymer layer are the same polymeric material.

The soft polymer layers of the appliances can have a variety of physical properties. For example, physical properties such as hardness, ultimate tensile strength, elongation at break, tensile modulus, compression set, flexural modulus, and light transmission can each be specifically tailored for a particular application. In some embodiments, the soft polymer layers of the appliances can independently have a physical property of at least one of a hardness of about 60 A to about 85 D, an ultimate tensile strength of greater than about 5000 psi, an elongation at break of greater than about 200%, a compression set at about 70° C. of greater than 40% after 24 hours, a flexural modulus of greater than about 35,000 psi, and a light transmission between 400 nm and 800 nm of greater than about 75%.

As described herein, the layers of the appliances can include a hard polymer layer disposed between two soft polymer layers. In one embodiment, the multilayer appliances can include a hard polymer layer of one type of material (e.g., a co-polyester), and two soft polymer layers of other types of material that can be the same or different (e.g., two soft polymer layers of thermoplastic polyurethane elastomer). In some embodiments, the multilayer appliances can also include a hard polymer layer of at least two layers of polymer material. For example, the hard polymer layer can include several polymer layers laminated together to form the hard polymer layer. The laminated hard polymer layer can include at least two layers of any combination of the following polymer materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and a polytrimethylene terephthalate. Similarly, in some embodiments, the multilayer appliances can include a soft polymer layer of at least two layers of polymer material. For example, the soft polymer layers 22, 26 can include a layer of several polymer layers 22-1, 22-2, 22-N and 26-1, 26-2, 26-N, respectively, laminated together. The laminated soft polymer layers can include at least two layers of any combination of the following polymer materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and a thermoplastic polyamide elastomer.

The tooth positioning appliances can be fabricated using a variety of methods. For example, methods for making the appliances can include thermoforming a multilayer sheet into an aligner by heating the sheet and then molding the sheet to a particular configuration. Exemplary methods for fabricating the appliances, including those utilized in the Invisalign® System, are described in numerous patents and patent applications assigned to Align Technology, Inc. including, for example, in U.S. application Ser. No. 13/186,374 as well as on the company's website, which is accessible on the World Wide Web (see, e.g., the url invisalign.com").

Figure 3:
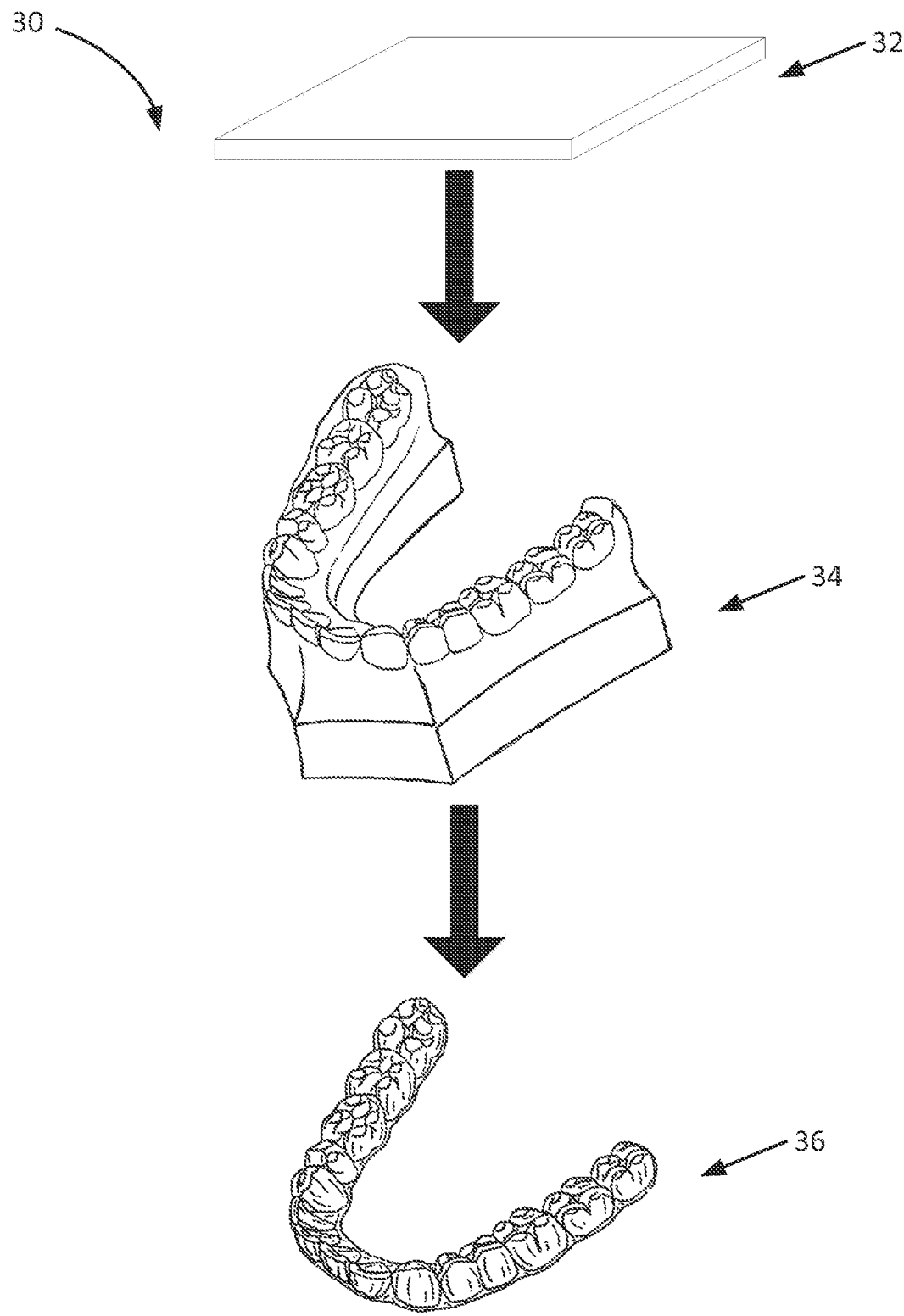
FIG. 3 depicts a method of making a multilayer dental appliance, in accordance with an embodiment of the present invention.

FIG. 3 depicts an example embodiment of a process 30 for forming a multilayer tooth positioning appliance, in accordance with an embodiment of the present invention. As shown, a multilayer sheet 32 can be formed into a tooth positioning appliance 36. The multilayer sheet 32, as depicted, can include three layers: a hard polymer layer disposed between two soft polymer layers. In this example process, the tooth positioning appliance 36 can be produced with the use of a physical tooth model, or mold, 34. The tooth positioning appliance 36 can be produced by heating the thermoformable multilayer sheet 32 and then vacuum or pressure forming the sheet over the teeth in the physical tooth model 34. The tooth positioning appliance 36 is a direct representation of the physical tooth model. Excess material from the sheet can be trimmed to form a final tooth positioning appliance that can be used for orthodontic treatment of a patient.

One or a series of physical tooth models, such as the model described above, may be used in the generation of elastic repositioning appliances for orthodontic treatment. Similar to the process above, each of the appliances can be generated by thermoforming a multilayer polymeric material over a mold of a desired tooth arrangement to form a dental appliance. The tooth positioning appliance of the desired tooth arrangement generally conforms to a patient's teeth but is slightly out of alignment with the initial tooth configuration. Placement of the elastic positioner over the teeth applies controlled forces in specific locations to gradually move the teeth into the desired configuration. Repetition of this process with successive appliances comprising new configurations eventually moves the teeth through a series of intermediate configurations to a final desired configuration.

Figure 4:
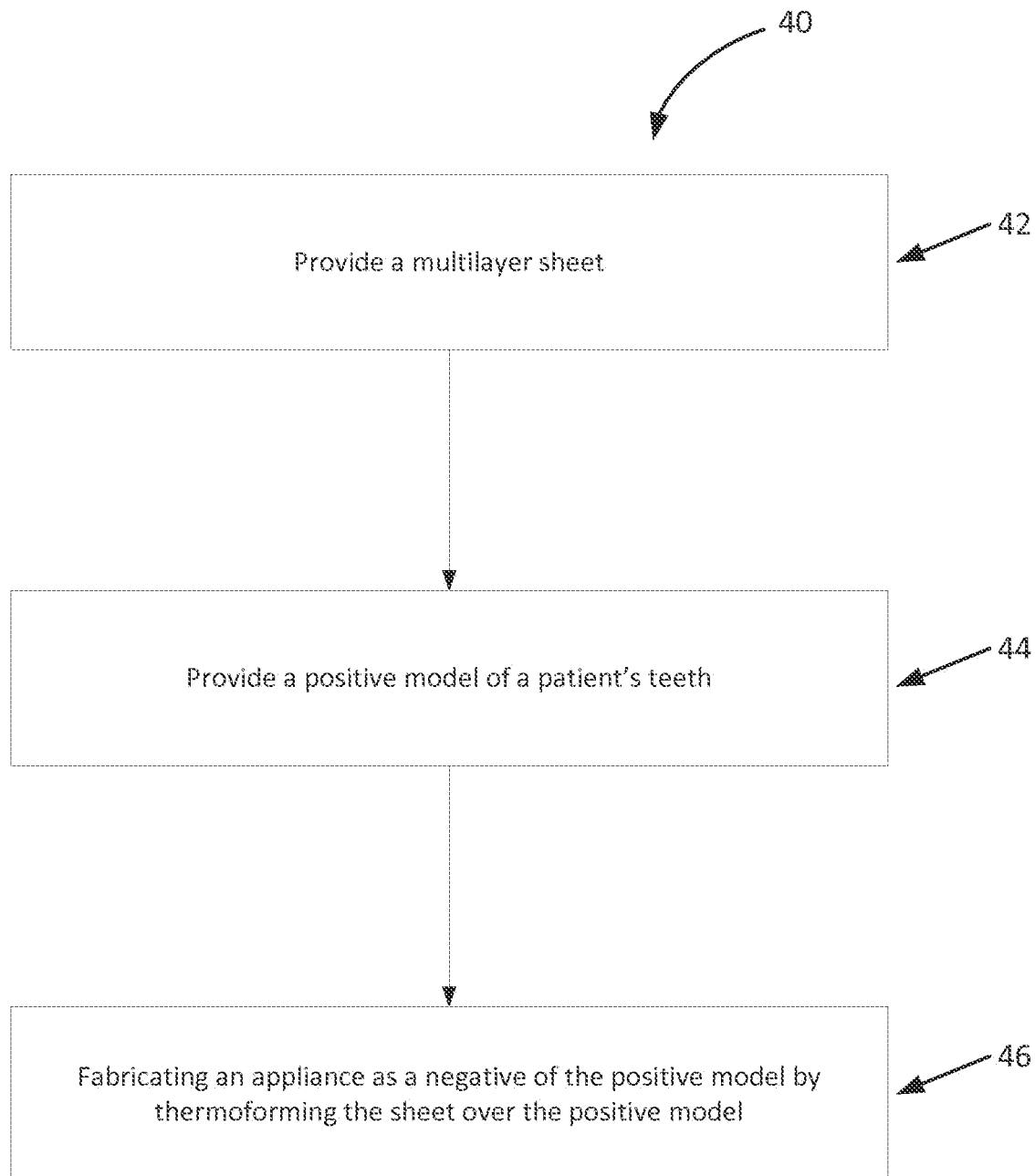
FIG. 4 is a simplified block diagram illustrating a method for fabricating a dental appliance, in accordance with an embodiment of the present invention.

The present invention includes a variety of methods for fabricating dental appliances. FIG. 4 shows a simple schematic for a method 40 of fabricating a removable orthodontic tooth positioning appliance having teeth receiving cavities shaped to directly receive at least some of the patient's teeth and apply a resilient positioning force to the patient's teeth, in accordance with an embodiment of the present invention. The method can include providing a multilayer sheet having a hard polymer layer disposed between two soft polymer layers (Step 42). The method can further include providing a positive physical model of a patient's teeth (Step 44). The tooth positioning appliance can be fabricated by thermoforming the multilayer sheet over the positive physical model (Step 46), in which the tooth positioning appliance is a negative of the positive model. As described above, the methods of fabrication can further include trimming or cutting portions of the sheet to render a final, usable appliance for orthodontic treatment.

Multilayer sheets of the present invention were analyzed and determined to provide a variety of improved properties for aligners used in orthodontic treatment. As further described herein, the multilayer sheets formed into aligners can, for example, provide increased durability of the aligners so that they can better withstand wear due to teeth grinding and other mechanical stresses put on the aligner during treatment. In addition, the aligners have improved elastic properties that allow for less degradation in the shape of the teeth receiving cavities during a stage of treatment. For example, during a multistage orthodontic treatment, the capability of an aligner to force tooth movement can degrade and may cause the treatment to include more aligners to reach a final ideal arrangement and/or result in a mid-course correction that could be prevented by using aligners with improved physical properties, such as those provided herein.

Figure 5:
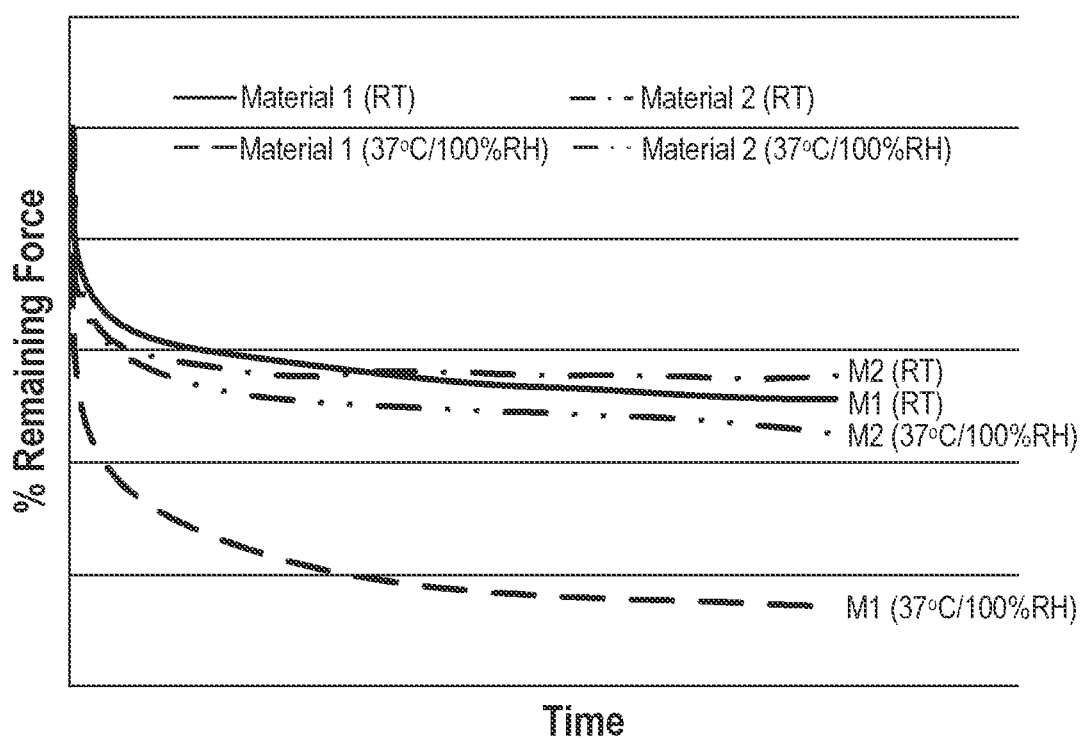
FIG. 5 provides a stress relaxation comparison for dental appliances, in accordance with an embodiment of the present invention.
Figure 6:
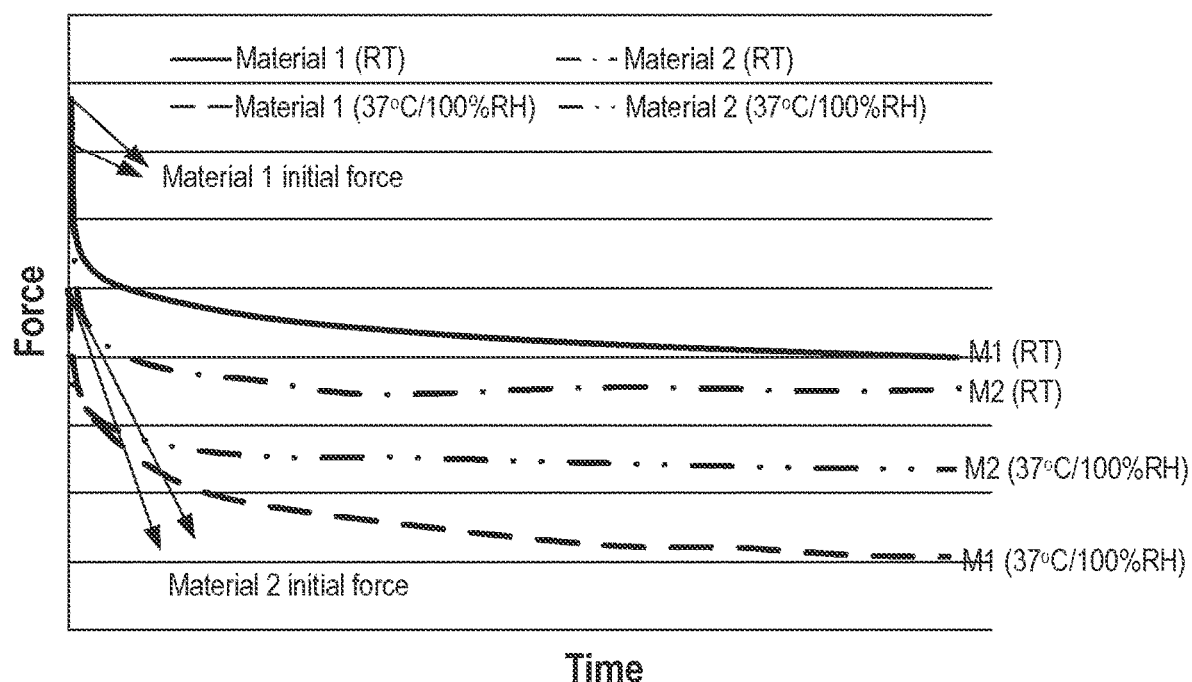
FIG. 6 provides another stress relaxation comparison for dental appliances, in accordance with an embodiment of the present invention.
Figure 7:
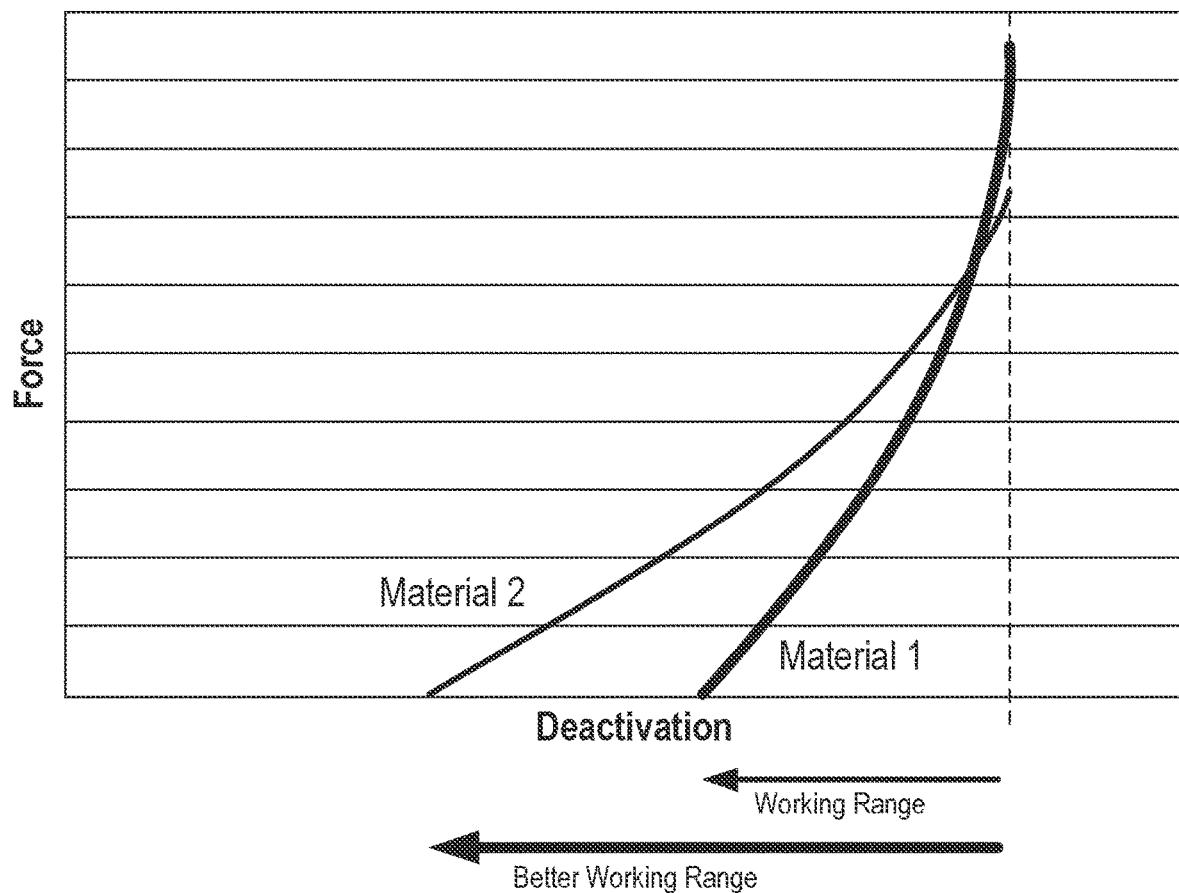
FIG. 7 shows a long-term unloading comparison for dental appliances, in accordance with an embodiment of the present invention.
Figure 8:
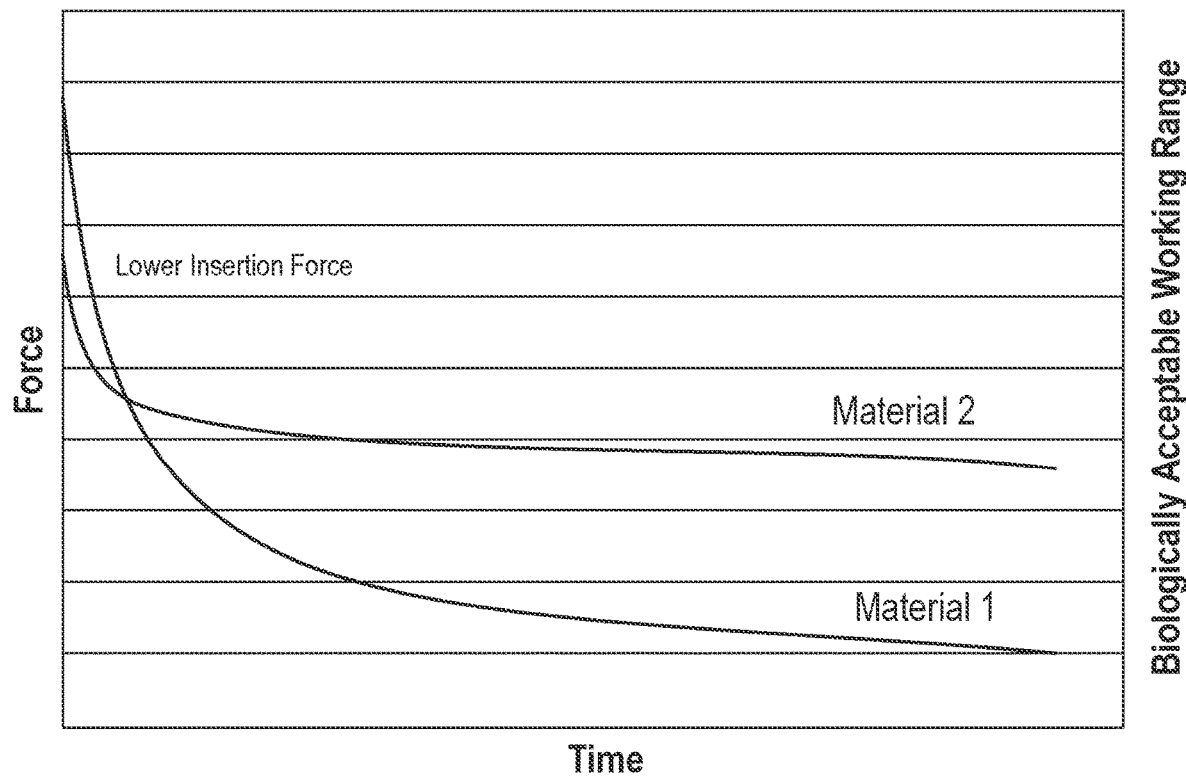
FIG. 8 provides a long-term movement comparison for dental appliances, in accordance with an embodiment of the present invention.

FIGS. 5-8 provide example test results that compare various physical properties of the multilayer sheet appliances of the present invention with other already existing aligner materials (Material 1). Samples of varied thicknesses were tested. For example, multilayer sheets were tested having a hard polymer layer with thicknesses ranging from about 580 µm to about 715 µm thick. In some examples, the hard layer was a co-polyester hard polymer layer. The soft layers tested ranged between about 50 µm to about 100 µm. In some examples, the hard polymer layer was disposed between thermoplastic polyurethane elastomer soft polymer layers. As shown in FIGS. 5 and 6, one example of the multilayer sheet material (Material 2) showed improved stress relaxation properties as compared to another already existing material (Material 1) at room temperature and at a 37° C./90-100% relative humidity condition. In addition, FIG. 7 shows improved long-term unloading characteristics of the multilayer sheet Material 2 versus the already existing Material 1 in a 37° C./90-100% relative humidity condition. The multilayer sheet showed less deflection under force loads. FIG. 8 also shows improved long-term movement data for the multilayer sheet Material 2 versus Material 1 in a 37° C./90-100% relative humidity condition.

The use of the terms "a" and "an" and "the" and similar referents in the context of describing embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope unless otherwise claimed. No language in the specification should be construed as indicating any non-claimed element as essential to the practice of at least one embodiment.

Variations of the embodiments described herein may become apparent to those of ordinary skill in the art upon reading the foregoing description. The inventors expect skilled artisans to employ such variations as appropriate, and the inventors intend for embodiments to be constructed otherwise than as specifically described herein. Accordingly, suitable embodiments include all modifications and equivalents of the subject matter recited in the claims appended hereto as permitted by applicable law. Moreover, any combination of the above-described elements in all possible variations thereof is contemplated as being incorporated into some suitable embodiment unless otherwise indicated herein or otherwise clearly contradicted by context. The scope of the invention should, therefore, be determined not with reference to the above description, but instead should be determined with reference to the pending claims along with their full scope or equivalents.

What is claimed is:

1. A method of making a multilayer dental aligner for positioning a patient's teeth from a first arrangement toward a second arrangement, the method comprising:
   providing a multilayer sheet comprising:
      a first layer;
      a second layer; and
      a third layer;
      wherein the first layer consists of a co-polyester, the co-polyester having an elongation at break of greater than 70%;
      wherein the second layer consists of a thermoplastic polyurethane elastomer, the thermoplastic polyurethane elastomer having an elongation at break of greater than 200% and a hardness of about 60 A to about 85 D; and
      wherein the first layer has a hardness greater than the hardness of the second layer;
   providing a mold;
   thermoforming the multilayer sheet over the mold to form a plurality of tooth-receiving cavities configured to receive and reposition the patient's teeth from the first arrangement toward the second arrangement; and
   trimming excess material from the thermoformed multilayer sheet to form the multilayer dental aligner.

2. The method of claim 1, wherein the co-polyester has a tensile strength at yield of between about 4000 psi and 6500 psi, and wherein the thermoplastic polyurethane elastomer has an ultimate tensile strength of greater than about 5000 psi.

3. The method of claim 1, wherein the thermoplastic polyurethane elastomer has a flexural modulus greater than 35,000 psi.

4. The method of claim 1, wherein the co-polyester has a flexural modulus greater than 150,000 psi.

5. The method of claim 1, wherein the co-polyester and the thermoplastic polyurethane elastomer both have a light transmission between 400 nm and 800 nm of greater than about 75%.

6. The method of claim 1, wherein the thermoplastic polyurethane elastomer has a compression set at about 70° C. of greater than 40% after 24 hours.

7. The method of claim 1, wherein the first layer is coextruded with or laminated to the third layer.

8. The method of claim 1, wherein the co-polyester has a stress relaxation at 24 hours in a wet environment of between 90-100% humidity of greater than 10%.

9. The method of claim 1, wherein the third layer comprises a same or different co-polyester.

10. The method of claim 1, wherein the third layer comprises a same or different thermoplastic polyurethane elastomer.

11. The method of claim 1, wherein the third layer has a hardness from 60 A to 85 D.

12. The method of claim 1, wherein the third layer is disposed between the first layer and the second layer.

13. The method of claim 1, wherein the first layer is disposed adjacent to the third layer.

14. The method of claim 1, wherein the multilayer sheet further comprises a fourth layer.

15. The method of claim 1, wherein the first layer is thicker than the second layer.

16. A multilayer dental aligner for positioning a patient's teeth from a first arrangement toward a second arrangement, the multilayer dental aligner comprising:
   a multilayer sheet comprising:
      a first layer;
      a second layer; and
      a third layer;
      wherein the first layer consists of a co-polyester, the co-polyester having an elongation at break of greater than 70%;
      wherein the second layer consists of a thermoplastic polyurethane elastomer, the thermoplastic polyurethane elastomer having an elongation at break of greater than 200% and a hardness of about 60 A to about 85 D; and
      wherein the first layer has a hardness greater than the hardness of the second layer; and
   wherein the multilayer sheet forms a plurality of tooth-receiving cavities configured to receive and reposition the patient's teeth from the first arrangement toward the second arrangement.

17. The multilayer dental aligner of claim 16, wherein the co-polyester has a tensile strength at yield of between about 4000 psi and 6500 psi, and wherein the thermoplastic polyurethane elastomer has an ultimate tensile strength of greater than about 5000 psi.

18. The multilayer dental aligner of claim 16, wherein the thermoplastic polyurethane elastomer has a flexural modulus greater than 35,000 psi.

19. The multilayer dental aligner of claim 16, wherein the co-polyester has a flexural modulus greater than 150,000 psi.

20. The multilayer dental aligner of claim 16, wherein the co-polyester and the thermoplastic polyurethane elastomer both have a light transmission between 400 nm and 800 nm of greater than about 75%.

21. The multilayer dental aligner of claim 16, wherein the thermoplastic polyurethane elastomer has a compression set at about 70° C. of greater than 40% after 24 hours.

22. The multilayer dental aligner of claim 16, wherein the first layer is coextruded with or laminated to the third layer.

23. The multilayer dental aligner of claim 16, wherein the co-polyester has a stress relaxation at 24 hours in a wet environment of between 90-100% humidity of greater than 10%.

24. The multilayer dental aligner of claim 16, wherein the third layer comprises a same or different co-polyester.

25. The multilayer dental aligner of claim 16, wherein the third layer comprises a same or different thermoplastic polyurethane elastomer.

26. The multilayer dental aligner of claim 16, wherein the third layer has a hardness from 60 A to 85 D.

27. The multilayer dental aligner of claim 16, wherein the third layer is disposed between the first layer and the second layer.

28. The multilayer dental aligner of claim 16, wherein the first layer is disposed adjacent to the third layer.

29. The multilayer dental aligner of claim 16, wherein the multilayer sheet further comprises a fourth layer.

30. The multilayer dental aligner of claim 16, wherein the first layer is thicker than the second layer.

* * * * *